(12) United States Patent
Kanno et al.

(10) Patent No.: US 9,864,028 B2
(45) Date of Patent: Jan. 9, 2018

(54) PET-MRI APPARATUS

(71) Applicants: NATIONAL INSTITUTE OF RADIOLOGICAL SCIENCES, Chiba-shi, Chiba (JP); TOSHIBA MEDICAL SYSTEMS CORPORATION, Otawara-shi, Tochigi (JP)

(72) Inventors: Iwao Kanno, Chiba (JP); Takayuki Obata, Chiba (JP); Taiga Yamaya, Chiba (JP); Kazuya Okamoto, Saitama (JP); Takuzo Takayama, Utsunomiya (JP); Hitoshi Yamagata, Otawara (JP)

(73) Assignees: National Institutes for Quantum and Radiological Science and Technology, Chiba (JP); Toshiba Medical Systems Corporation, Otawara-shi, Tochigi (JP)

(*) Notice: Subject to any disclaimer, the term of this patent is extended or adjusted under 35 U.S.C. 154(b) by 1290 days.

(21) Appl. No.: 13/873,706

(22) Filed: Apr. 30, 2013

(65) Prior Publication Data
US 2013/0234710 A1 Sep. 12, 2013

Related U.S. Application Data

(63) Continuation of application No. PCT/JP2011/074990, filed on Oct. 28, 2011.

(30) Foreign Application Priority Data

Nov. 1, 2010 (JP) .................................. 2010-245605

(51) Int. Cl.
G01R 33/422 (2006.01)
A61B 5/055 (2006.01)
(Continued)

(52) U.S. Cl.
CPC .......... *G01R 33/422* (2013.01); *A61B 5/0035* (2013.01); *A61B 5/055* (2013.01);
(Continued)

(58) Field of Classification Search
CPC .. G01R 33/422; G01R 33/481; A61B 5/0035; A61B 5/055; A61B 6/5247; A61B 6/5235; A61B 6/4417; A61B 6/037; G01T 1/1603
See application file for complete search history.

(56) References Cited

U.S. PATENT DOCUMENTS 6,961,604 B1  11/2005 Vahasalo et al.
7,323,874 B2 *  1/2008 Krieg .................... G01T 1/1603
                                                              324/318
(Continued)

FOREIGN PATENT DOCUMENTS

CN        1839757 A        10/2006
JP       2005-505361        2/2005
(Continued)

OTHER PUBLICATIONS

International Search Report for PCT/JP2011/074990 dated Jan. 10, 2012.
(Continued)

*Primary Examiner* — Dixomara Vargas
(74) *Attorney, Agent, or Firm* — Nixon & Vanderhye P.C.

(57) ABSTRACT

In a PET (Positron Emission Tomography)-MRI (Magnetic Resonance Imaging) apparatus of an embodiment, a transmitting radio frequency coil applies a radio frequency magnetic field on a subject placed in a static magnetic field. A detector is formed in a ring shape, disposed on a side adjacent to an outer circumference of the transmitting radio frequency coil, includes at least two PET detectors disposed with a space therebetween in an axial direction of a bore so
(Continued)

as to interpose the magnetic field center of the static magnetic field therebetween, and detects gamma rays emitted from positron emitting radionuclides injected into the subject. Radio frequency shields are each formed in an approximately cylindrical shape, disposed between the transmitting radio frequency coil and the detector, and shield the radio frequency magnetic field generated by the transmitting radio frequency coil.

7 Claims, 7 Drawing Sheets

(51) Int. Cl.
    *A61B 6/03*     (2006.01)
    *A61B 6/00*     (2006.01)
    *G01R 33/48*     (2006.01)
    *G01T 1/16*     (2006.01)
    *A61B 5/00*     (2006.01)

(52) U.S. Cl.
    CPC ............ *A61B 6/037* (2013.01); *A61B 6/4417* (2013.01); *A61B 6/5235* (2013.01); *A61B 6/5247* (2013.01); *G01R 33/481* (2013.01); *G01T 1/1603* (2013.01)

(56) References Cited

U.S. PATENT DOCUMENTS

| | | | |
|---|---|---|---|
| 8,131,340 B2 * | 3/2012 | Eberlein | G01R 33/34046 600/407 |
| 9,121,893 B2 * | 9/2015 | Schmand | G01R 33/26 |
| 2006/0238198 A1 | 10/2006 | Nabetani | |
| 2007/0102641 A1 | 5/2007 | Schmand et al. | |
| 2008/0137930 A1 * | 6/2008 | Rosen | G06T 11/005 382/131 |
| 2008/0208035 A1 | 8/2008 | Nistler et al. | |
| 2008/0265887 A1 * | 10/2008 | Linz | G01R 33/28 324/318 |
| 2009/0209844 A1 | 8/2009 | Gagnon et al. | |
| 2010/0033186 A1 | 2/2010 | Overweg et al. | |
| 2010/0217112 A1 * | 8/2010 | Choi | A61B 5/05 600/411 |
| 2010/0219347 A1 * | 9/2010 | Schulz | G01T 1/1603 250/363.04 |
| 2012/0150017 A1 | 6/2012 | Yamaya et al. | |
| 2012/0161014 A1 | 6/2012 | Yamaya et al. | |

FOREIGN PATENT DOCUMENTS

| | | |
|---|---|---|
| JP | 2006/296826 | 11/2006 |
| JP | 2008-525161 | 7/2008 |
| JP | 2008-206977 | 9/2008 |
| JP | 2010-508079 | 3/2010 |
| JP | 2010/523191 | 7/2010 |
| JP | 2012-517848 | 8/2012 |
| WO | WO 2010/103644 | 9/2010 |
| WO | WO 2010/103645 | 9/2010 |

OTHER PUBLICATIONS

Office Action dated Mar. 13, 2014 in CN 201180004166.5.
Office Action dated Sep. 24, 2014, in JP 2010-245605 with English translation.

* cited by examiner

PET-MRI APPARATUS

CROSS-REFERENCE TO RELATED APPLICATIONS

This application is a continuation of PCT international application Ser. No. PCT/JP2011/074990 filed on Oct. 28, 2011 which designates the United States, and which claims the benefit of priority from Japanese Patent Application No. 2010-245605, filed on Nov. 1, 2010; the entire contents of which are incorporated herein by reference.

FIELD

Embodiments described herein relate generally to a PET (Positron Emission Tomography)-MRI (Magnetic Resonance Imaging) apparatus.

BACKGROUND

In many cases, MRI apparatuses have been utilized to inspect cephalic regions, for example. It has been also expected that PET apparatuses are utilized to inspect cephalic regions, e.g., to diagnose Alzheimer diseases. Hence, recently, it has been expected to realize a PET-MRI apparatus combining a PET apparatus and an MRI apparatus.

The MRI apparatuses, however, have some limitations. For example, a photomultiplier tube (PMT) used as a detector of a conventional PET apparatus cannot be used when the PET-MRI apparatus is intended to be realized because a strong radio frequency magnetic field is used in the MRI apparatus. Therefore, a PET-MRI apparatus has been proposed that uses an APD (Avalanche Photodiode) or a SiPM (Silicon Photomultiplier) instead of the PMT, for example.

In some conventional PET-MRI apparatuses, an SNR (Signal-to-Noise Ratio) of an MR image is lowered due to the interference between a detector and signal lines that are elements of the PET apparatus and a transmitting radio frequency coil that is an element of the MRI apparatus.

DETAILED DESCRIPTION

A PET-MRI apparatus according to an embodiment includes a magnet, a transmitting radio frequency coil, a gradient coil, a receiving radio frequency coil, an MR image reconstruction unit, a detector, a PET image reconstruction unit, and a radio frequency shield. The magnet is configured to generate a static magnetic field in a bore having an approximately cylindrical shape. The transmitting radio frequency coil is configured to apply a radio frequency magnetic field on a subject placed in the static magnetic field. The gradient coil is configured to apply a gradient magnetic field on the subject. The receiving radio frequency coil is configured to detect a magnetic resonance signal emitted from the subject due to application of the radio frequency magnetic field and the gradient magnetic field on the subject. The MR image reconstruction unit is configured to reconstruct an MR image based on the magnetic resonance signal detected by the receiving radio frequency coil. The detector is configured to be formed in a ring shape, disposed on a side adjacent to an outer circumference of the transmitting radio frequency coil, include at least two PET detectors disposed with a space therebetween in an axial direction of the bore so as to interpose a magnetic field center of the static magnetic field therebetween, and detect gamma rays emitted from a positron emitting radionuclide injected into the subject. The PET image reconstruction unit is configured to reconstruct a PET image from projection data produced based on the gamma rays detected by the detector. The radio frequency shield is configured to have an approximately cylindrical shape, be disposed between the transmitting radio frequency coil and the detector, and shield a radio frequency magnetic field generated by the transmitting radio frequency coil.

Embodiments of a PET-MRI apparatus are described in detail below with reference to the accompanying drawings.

First Embodiment

Figure 1:
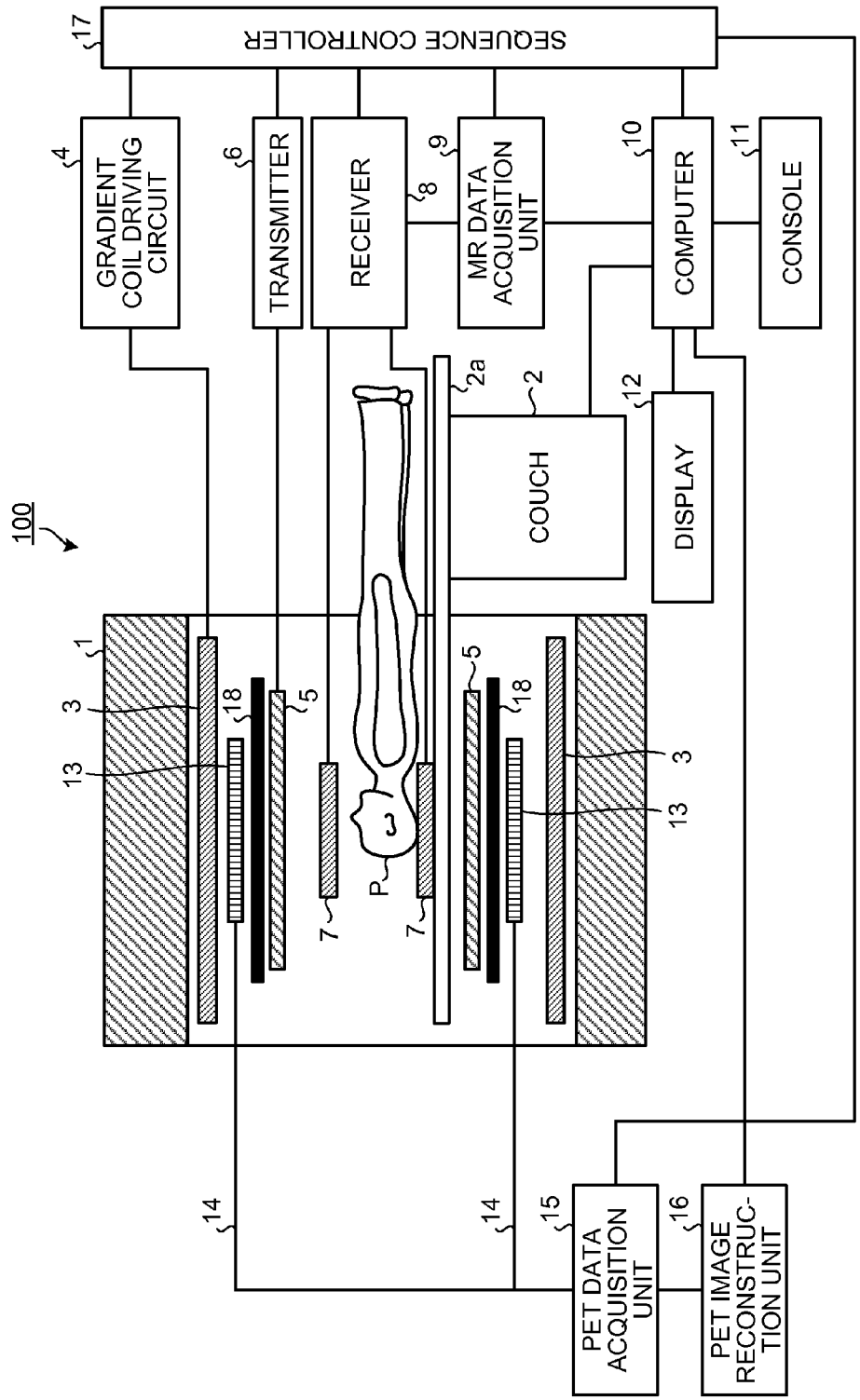
FIG. 1 is a schematic illustrating a structure of a PET-MRI apparatus according to a first embodiment.

First, a structure of a PET-MRI apparatus according to a first embodiment is described. FIG. 1 is a schematic illustrating a structure of a PET-MRI apparatus 100 according to the first embodiment. As illustrated in FIG. 1, the PET-MRI apparatus 100 includes a magnet 1, a couch 2, a gradient coil 3, a gradient coil driving circuit 4, a transmitting radio frequency coil 5, a transmitter 6, a receiving radio frequency coil 7, a receiver 8, an MR data acquisition unit 9, a computer 10, a console 11, a display 12, a PET detector 13, signal lines 14, a PET data acquisition unit 15, a PET image reconstruction unit 16, a sequence controller 17, and a radio frequency shield 18.

The magnet 1 generates a static magnetic field in a bore having an approximately cylindrical shape. The bore is formed as the inner wall of a gantry having an approximately cylindrical shape and housing the magnet 1, the gradient coil 3, and the like. The couch 2 has a couchtop 2a on which a subject P is placed. The couch 2 moves the couchtop 2a into an inside of the bore when the subject P is imaged, so that the subject P is moved in the static magnetic field.

The gradient coil 3 applies gradient magnetic fields Gx, Gy, and Gz on the subject P. The magnetic field intensities of the gradient magnetic fields Gx, Gy, and Gz change linearly in the X, Y, and Z directions, respectively. The gradient coil 3 is formed in an approximately cylindrical shape and disposed on a side adjacent to an inner circumference of the magnet 1. The gradient coil driving circuit 4 drives the gradient coil 3 under control of the sequence controller 17.

The transmitting radio frequency coil 5 applies a radio frequency magnetic field on the object P placed in the static magnetic field based on a radio frequency pulse transmitted from the transmitter 6. The transmitting radio frequency coil 5 is formed in an approximately cylindrical shape and disposed on a side adjacent to an inner circumference of the gradient coil 3. The transmitter 6 transmits the radio frequency pulse to the transmitting radio frequency coil 5 under control of the sequence controller 17.

The receiving radio frequency coil 7 detects a magnetic resonance signal emitted from the object P due to the application of the radio frequency magnetic field and the gradient magnetic field on the object P. For example, the receiving radio frequency coil 7 is a surface coil disposed on a surface of the object P corresponding to a region to be imaged. For example, when a body region of the object P is imaged, two receiving radio frequency coils 7 are disposed on the upper side and the lower side of the object P. The receiver 8 receives the magnetic resonance signal detected by the receiving radio frequency coil 7 under control of the sequence controller 17. The receiver 8 transmits the received magnetic resonance signal to the MR data acquisition unit 9.

The MR data acquisition unit 9 acquires the magnetic resonance signal sent from the receiver 8 under control of the sequence controller 17. The MR data acquisition unit 9 amplifies the acquired magnetic resonance signal and performs detection on the amplified signal. Thereafter, the MR data acquisition unit 9 A/D-converts the signal after the detection and sends the converted signal to the computer 10. The computer 10, which is controlled with the console 11, reconstructs an MR image based on the magnetic resonance signal sent from the MR data acquisition unit 9. The computer 10 allows the display 12 to display the reconstructed MR image.

The PET detector 13 detects, as counting information, gamma rays (including annihilation radiation) emitted from positron emitting radionuclides injected into the subject P. The PET detector 13 is formed in a ring shape and disposed on a side adjacent to an outer circumference of the transmitting radio frequency coil 5. For example, the PET detector 13 is formed by arranging detector modules including scintillators and photo detectors in a ring shape. Examples of the scintillator include LYSO (Lutetium Yttrium Oxyorthosilicate), LSO (Lutetium Oxyorthosilicate), and LGSO (Lutetium Gadolinium Oxyorthosilicate). Examples of the photo detector include an APD (Avalanche Photodiode) element and a SiPM (Silicon Photomultiplier). The PET detector 13 sends the detected counting information to the PET data acquisition unit 15 through the signal lines 14.

The PET data acquisition unit 15 produces simultaneous counting information under control of the sequence controller 17. The PET data acquisition unit 15 produces, as the simultaneous counting information, a combination of counting information of the gamma rays that are emitted from the positron emitting radionuclides and approximately simultaneously detected by using the counting information of gamma rays detected by the PET detector 13.

The PET image reconstruction unit 16 reconstructs a PET image by using the simultaneous counting information produced by the PET data acquisition unit 15 as projection data. The PET image reconstructed by the PET image reconstruction unit 16 is transmitted to the computer 10 and displayed on the display 12. The sequence controller 17 receives from the computer 10 various imaging sequence information executed when the subject is imaged and controls the above-described elements.

In the first embodiment having the structure thus described, the radio frequency shield 18 formed in an approximately cylindrical shape is disposed between the transmitting radio frequency coil 5 and the PET detector 13. That is, the radio frequency shield 18 is disposed on a side adjacent to an inner circumference of the PET detector 13 and shields a radio frequency magnetic field generated by the transmitting radio frequency coil 5. This results in the PET detector 13 not being exposed to the radio frequency magnetic field. As a result, loss in the radio frequency magnetic field can be suppressed.

Figure 2:
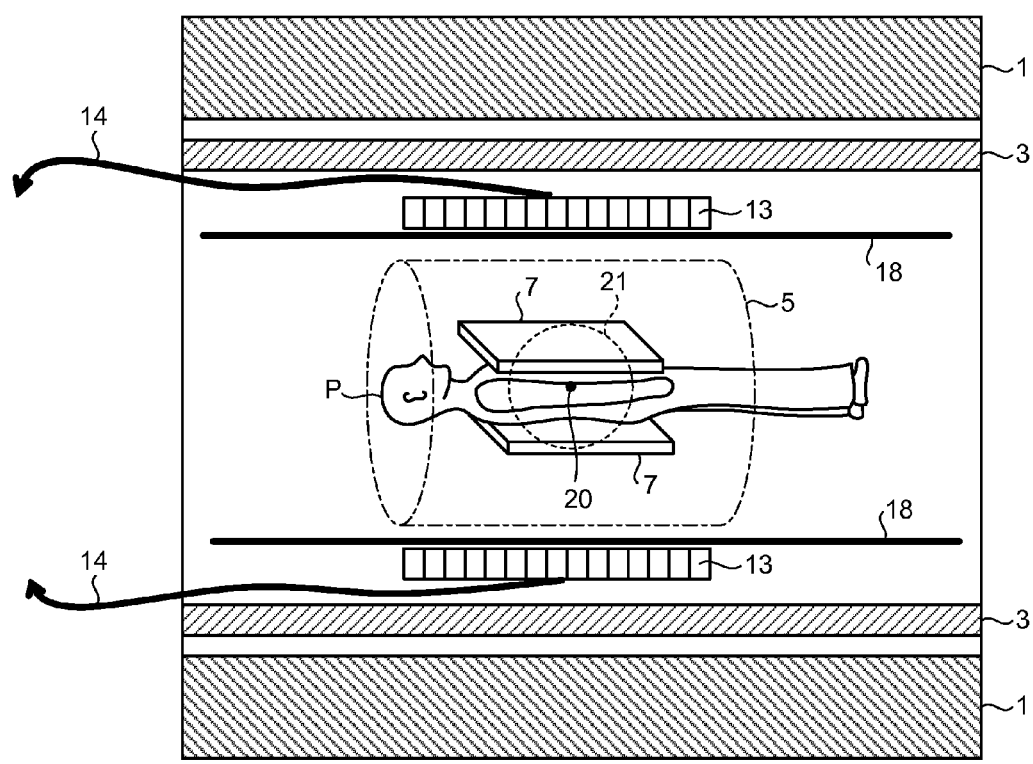
FIG. 2 is a schematic illustrating an element arrangement at a periphery of a PET detector according to the first embodiment.

An element arrangement at a periphery of the PET detector 13 is described below. FIG. 2 is a schematic illustrating the element arrangement at the periphery of the PET detector 13 according to the first embodiment.

As illustrated in FIG. 2, the gradient coil 3 is disposed on the side adjacent to the inner circumference of the magnet 1 in the first embodiment. The radio frequency shield 18 is disposed on a side adjacent to an inner circumference of the gradient coil 3 so as to interpose the PET detector 13 between itself and the gradient coil 3. The transmitting radio frequency coil 5 and the receiving radio frequency coil 7 are disposed on a side adjacent to an inner circumference of the radio frequency shield 18. A dot 20 illustrated in FIG. 2 represents the magnetic field center of the static magnetic field. A region 21 surrounded with the dashed line in FIG. 2 represents an effective imaging region of the MR image.

The arrangement in which the PET detector 13 is disposed between the radio frequency shield 18 and the gradient coil 3 can prevent the interference between the radio frequency magnetic field generated by the transmitting radio frequency coil 5 and the PET detector 13.

As illustrated in FIG. 2, the signal lines 14 connected to the PET detector 13 are routed on a side adjacent to an outer circumference of the radio frequency shield 18 in the first embodiment. The signal lines 14 transmit a signal output from the PET detector 13 and a control signal input to the PET detector 13, for example. This arrangement can prevent the interference between the radio frequency magnetic field generated by the transmitting radio frequency coil 5 and signals transmitted through the signals lines 14.

As described above, the PET-MRI apparatus 100 according to the first embodiment includes the magnet 1, the transmitting radio frequency coil 5, the gradient coil 3, the receiving radio frequency coil 7, the computer 10, the PET detector 13, the PET image reconstruction unit 16, and the radio frequency shield 18. The magnet 1 generates the static magnetic field in the bore having an approximately cylindrical shape. The transmitting radio frequency coil 5 applies the radio frequency magnetic field on the subject P placed in the static magnetic field. The gradient coil 3 applies the gradient magnetic field on the subject P. The receiving radio frequency coil 7 detects the magnetic resonance signal emitted from the subject P due to the application of the radio frequency magnetic field and the gradient magnetic field on the subject P. The computer 10 reconstructs the MR image based on the magnetic resonance signal detected by the receiving radio frequency coil 7. The PET detector 13 is formed in a ring shape, disposed on the side adjacent to the outer circumference of the transmitting radio frequency coil 5, and detects the gamma rays emitted from positron emitting radionuclides injected into the subject P. The PET image reconstruction unit 16 reconstructs the PET image from projection data produced based on the gamma rays detected by the PET detector 13. The radio frequency shield 18 is formed in an approximately cylindrical shape, disposed between the transmitting radio frequency coil 5 and the PET detector 13, and shields the radio frequency magnetic field generated by the transmitting radio frequency coil 5. The structure in which the PET detector 13 is disposed between the radio frequency shield 18 and the gradient coil 3 can prevent the interference between the radio frequency magnetic field generated by the transmitting radio frequency coil 5 and the PET detector 13. As a result, according to the first embodiment, deterioration of image quality of the MR image due to the interference between the PET detector and the transmitting radio frequency coil can be suppressed.

Second Embodiment

The element arrangement at the periphery of the PET detector 13 is not limited to that illustrated in FIG. 2.

Another element arrangement at the periphery of the PET detector 13 is described below as a second embodiment. FIGS. 3 to 7 are schematics each illustrating the element arrangement at the periphery of the PET detector 13 according to the second embodiment.

Figure 3:
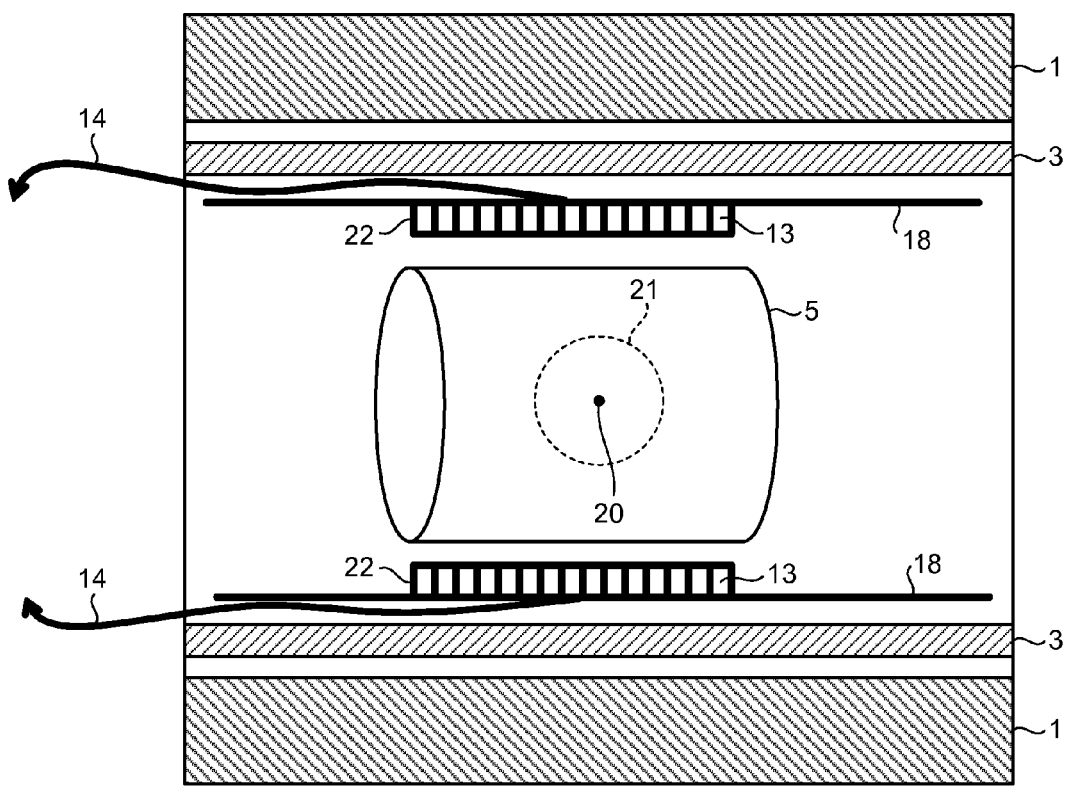
FIGS. 3 to 7 are schematics each illustrating the element arrangement at the periphery of the PET detector according to the second embodiment.

As illustrated in FIG. 3, the radio frequency shield 18 may be disposed on a side adjacent to an outer circumference of the PET detector 13, for example. In this case, the PET detector 13 is electrically connected to the inner wall of the radio frequency shield 18. In addition, a radio frequency shield 22 is formed on a surface of the PET detector 13 so as to cover an exposed surface of the PET detector 13. As a result, the interference between the radio frequency magnetic field generated by the transmitting radio frequency coil 5 and the PET detector 13 can be prevented. In addition, the inner diameter of the radio frequency shield 18 is larger than that of the arrangement illustrated in FIG. 2, allowing a large space to be provided near an opening of the bore. This large space can alleviate a cooped-up feeling of the subject P.

Figure 4:
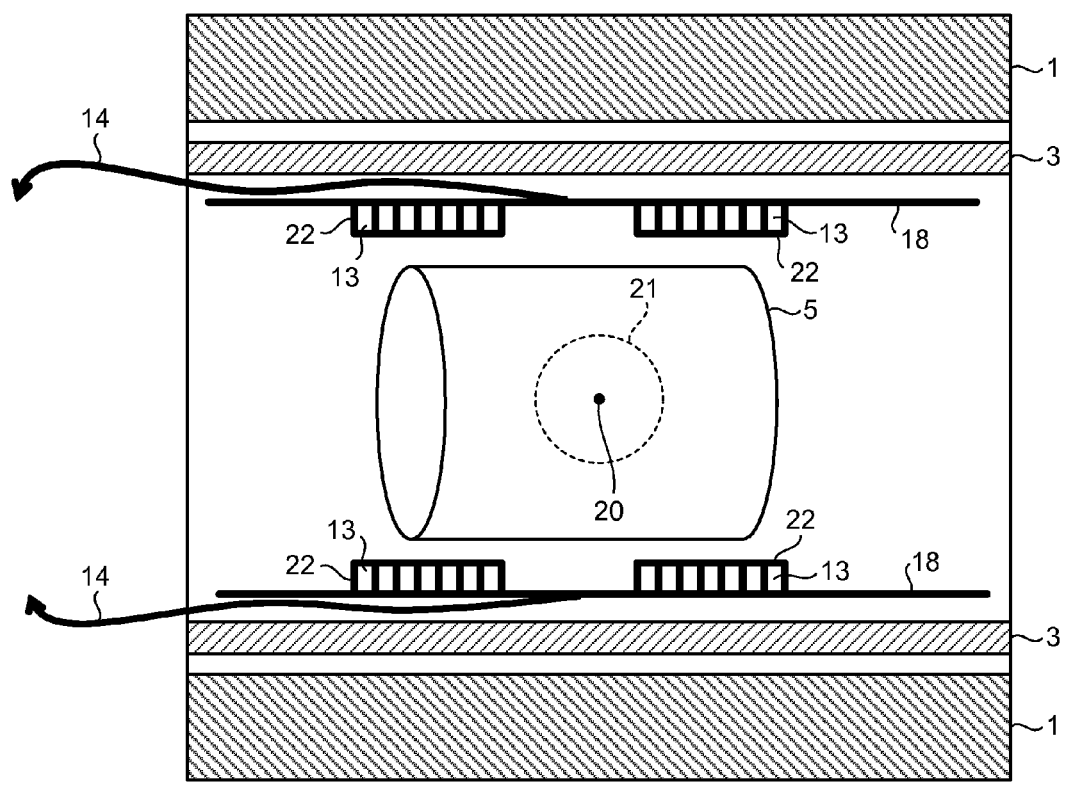

As illustrated in FIG. 4, two PET detectors 13 may be disposed with a space therebetween in an axial direction of the bore so as to interpose the magnetic field center 20 of the static magnetic field therebetween, for example. Generally, when the radio frequency shield 18 is disposed near the transmitting radio frequency coil 5, intensity of the radio frequency magnetic field effective for taking the MR image is weakened by a radio frequency current passively flowing in the radio frequency shield 18. In contrast, in the arrangement illustrated in FIG. 4, the PET detectors 13 are not disposed near the magnetic field center 20 of the static magnetic field, allowing a distance between the radio frequency shield 18 and the transmitting radio frequency coil 5 to be ensured at a central area of the magnet 1. As a result, lowering of the intensity of the radio frequency magnetic field in the effective imaging region 21 of the MR image can be prevented. In FIG. 4, two PET detectors 13 are disposed. However, the number of PET detectors 13 may be three or more.

Figure 5:
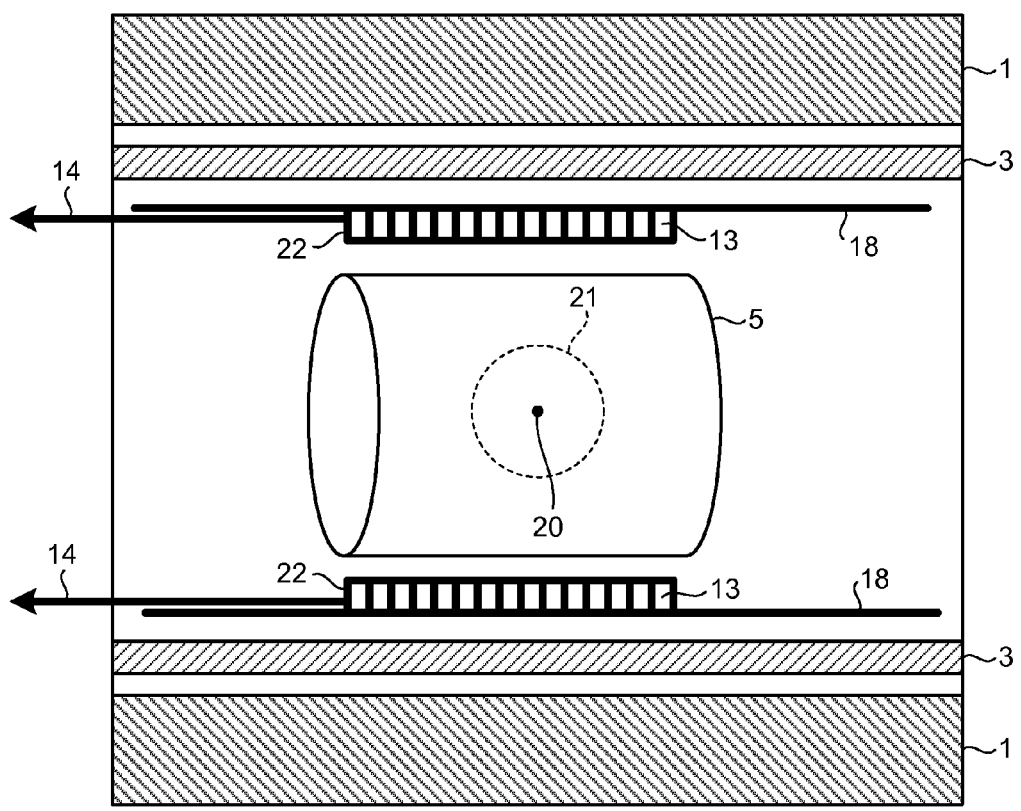
Figure 6:
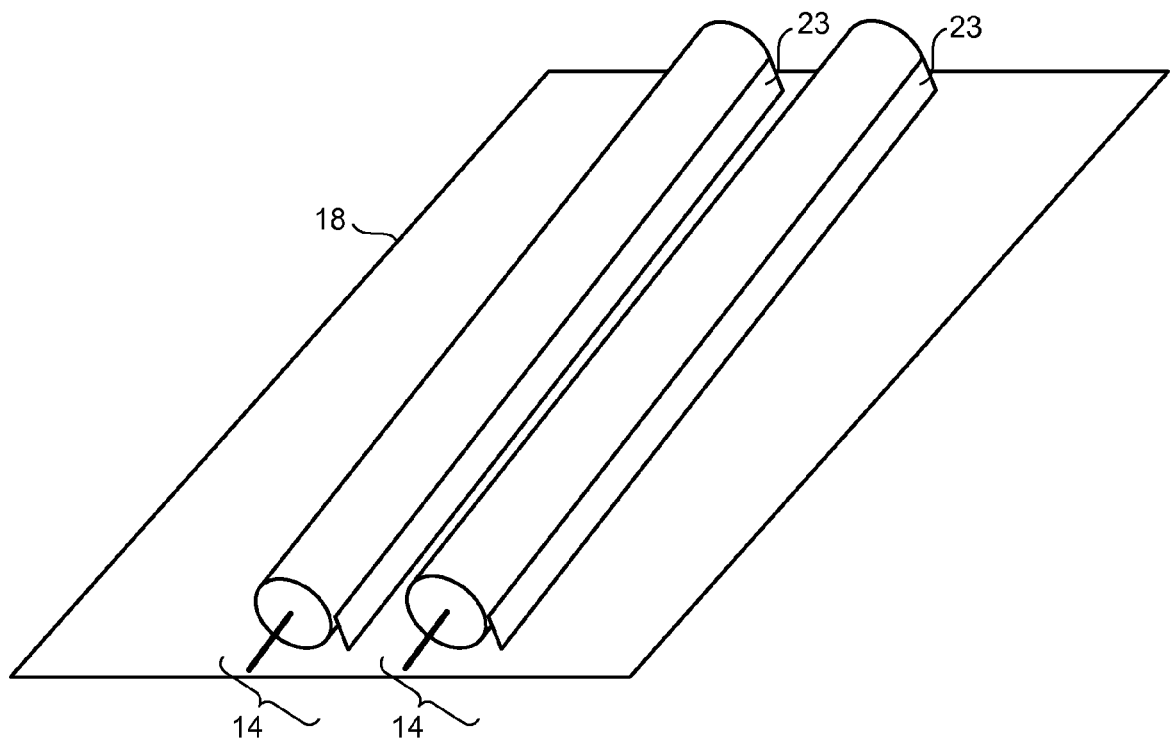
Figure 7:
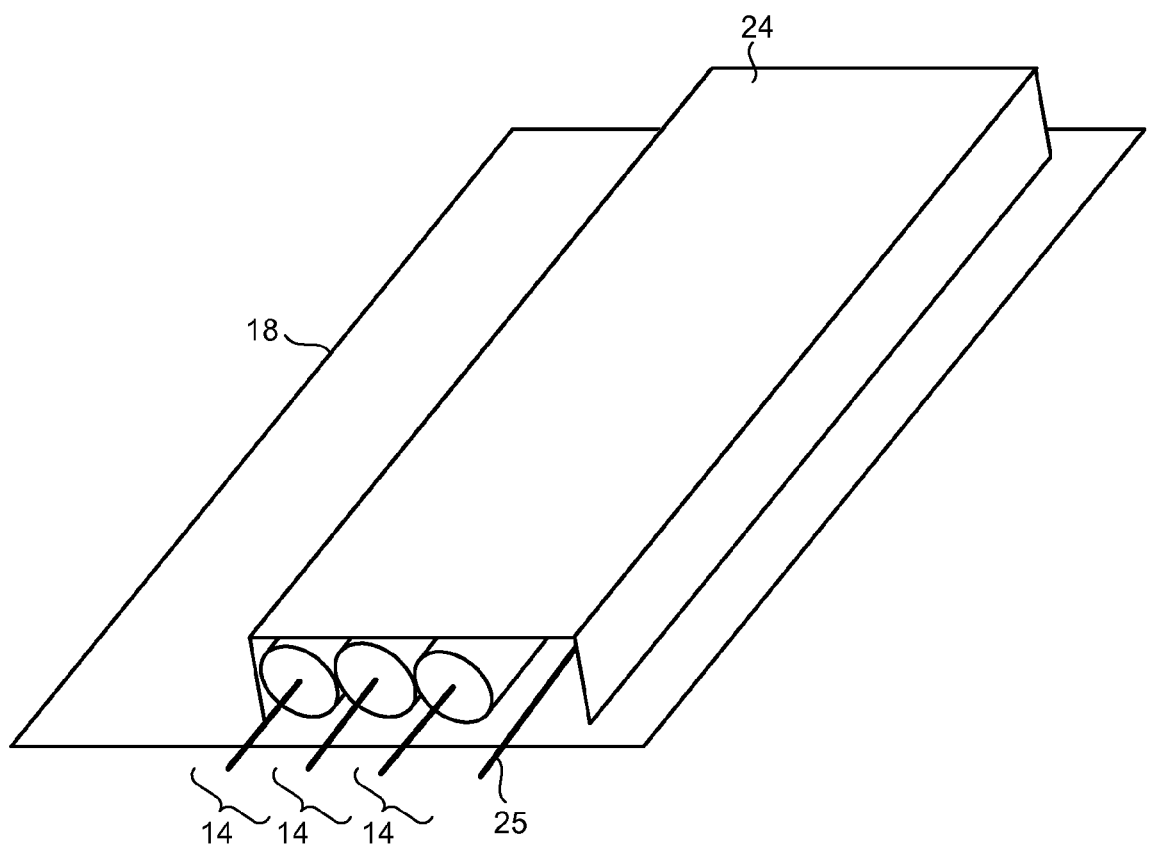

As illustrated in FIG. 5, the signal lines 14 connected to the PET detector 13 may be routed on the side adjacent to the inner circumference of the radio frequency shield 18, for example. In this case, when the signal lines 14 are coaxial cables, for example, the outer conductors of the coaxial cables are electrically connected to the radio frequency shield 18 as illustrated in FIG. 6. For example, the outer conductors of the coaxial cables are coupled to the radio frequency shield 18 with connectors 23 made of conductors interposed therebetween. The connector 23 is made of solder, for example. As a result, the interference between the signals transmitted through the signal lines 14 and the radio frequency magnetic field can be prevented. As illustrated in FIG. 7, a radio frequency shield 24 may be formed so as to cover the signal lines 14, for example. In this case, even when a signal line 25, which is not the coaxial cable, is used, the interference between signals transmitted through the signal line 25 and the radio frequency magnetic field can be prevented.

As described above, according to the first or the second embodiment, the PET-MRI apparatus can be realized that can suppress the deterioration of image quality of the MR image due to the influence between the PET detector and the transmitting radio frequency coil.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A PET (Positron Emission Tomography)-MRI (Magnetic Resonance Imaging) apparatus, comprising:
    a magnet configured to generate a static magnetic field in a bore having an approximately cylindrical shape;
    a transmitting radio frequency coil configured to apply a radio frequency magnetic field on a subject placed in the static magnetic field;
    a gradient coil configured to apply a gradient magnetic field on the subject;
    a receiving radio frequency coil configured to detect a magnetic resonance signal emitted from the subject due to application of the radio frequency magnetic field and the gradient magnetic field on the subject;
    an MR image reconstruction unit configured to reconstruct an MR image based on the magnetic resonance signal detected by the receiving radio frequency coil;
    a detector configured to be formed in a ring shape, disposed on a side adjacent to an outer circumference of the transmitting radio frequency coil, include at least two PET detectors disposed with a space therebetween in an axial direction of the bore so as to interpose a magnetic field center of the static magnetic field therebetween, and detect gamma rays emitted from a positron emitting radionuclide injected into the subject;
    a PET image reconstruction unit configured to reconstruct a PET image from projection data produced based on the gamma rays detected by the detector; and
    a radio frequency shield configured to have an approximately cylindrical shape, be disposed between the transmitting radio frequency coil and the detector, and shield a radio frequency magnetic field generated by the transmitting radio frequency coil.

2. The PET-MRI apparatus according to claim 1, wherein the radio frequency shield is disposed on a side adjacent to an inner circumference of the detector.

3. The PET-MRI apparatus according to claim 2, wherein a signal line connected to the detector is routed on a side adjacent to an outer circumference of the radio frequency shield.

4. The PET-MRI apparatus according to claim 1, further comprising:
    a first radio frequency shield configured to have an approximately cylindrical shape and be disposed on a side adjacent to an outer circumference of the detector; and
    a second radio frequency shield configured to be formed so as to cover an exposed surface of the detector.

5. The PET-MM apparatus according to claim 4, wherein a signal line connected to the detector is routed on a side adjacent to an outer circumference of the first radio frequency shield.

6. The PET-MRI apparatus according to claim 4, wherein the signal line connected to the detector is routed on a side adjacent to an inner circumference of the first radio frequency shield, and
    the signal line is a coaxial cable and an outer conductor of the coaxial cable is electrically connected to the first radio frequency shield.

7. The PET-MRI apparatus according to claim 4, wherein the signal line connected to the detector is routed on a side adjacent to an inner circumference of the first radio frequency shield, and
the signal line is covered with a third radio frequency shield.

* * * * *

UNITED STATES PATENT AND TRADEMARK OFFICE
CERTIFICATE OF CORRECTION

PATENT NO. : 9,864,028 B2  
APPLICATION NO. : 13/873706  
DATED : January 9, 2018  
INVENTOR(S) : Kanno et al.

Page 1 of 1

It is certified that error appears in the above-identified patent and that said Letters Patent is hereby corrected as shown below:

On the Title Page

(71) Applicants should read: NATIONAL INSTITUTES FOR QUANTUM AND RADIOLOGICAL SCIENCE AND TECHNOLOGY, Chiba (JP); TOSHIBA MEDICAL SYSTEMS CORPORATION, Otawara-shi Tochigi (JP)

Signed and Sealed this
Tenth Day of April, 2018

Andrei Iancu
*Director of the United States Patent and Trademark Office*